United States Patent [19]

Rajappa et al.

[11] 4,386,097

[45] * May 31, 1983

[54] BENZIMIDAZOLES, PROCESSES FOR THEIR PREPARATION AND PHARMACEUTICAL PREPARATIONS CONTAINING SUCH COMPOUNDS

[75] Inventors: Srinivasachari Rajappa; Vasudevan Sudarsanam, both of Bombay, India

[73] Assignee: Ciba-Geigy Corporation, Ardsley, N.Y.

[*] Notice: The portion of the term of this patent subsequent to Oct. 27, 1998, has been disclaimed.

[21] Appl. No.: 288,078

[22] Filed: Jul. 29, 1981

Related U.S. Application Data

[63] Continuation of Ser. No. 61,097, Jul. 26, 1979, Pat. No. 4,297,365.

[51] Int. Cl.$^3$ .................. C07D 519/00; A61K 31/425
[52] U.S. Cl. .................................... 424/270; 548/181
[58] Field of Search ......................... 548/181; 424/270

[56] References Cited

U.S. PATENT DOCUMENTS 4,026,936  5/1977  Lauer .
4,139,626  2/1979  Beard .
4,191,764  3/1980  Beard .
4,297,365  10/1981  Rajappa .

FOREIGN PATENT DOCUMENTS 2635326  7/1980  Fed. Rep. of Germany .

*Primary Examiner*—Robert Gerstl
*Attorney, Agent, or Firm*—Michael W. Glynn; Prabodh I. Almaula

[57] ABSTRACT

The invention relates to 2-carboethoxyamino-5(6)-(2-amino-5-thiazoloyl)-benzimidazole compounds with anthelmintic properties and to processes for their preparation and pharmaceutical preparations containing such compounds.

3 Claims, No Drawings

BENZIMIDAZOLES, PROCESSES FOR THEIR PREPARATION AND PHARMACEUTICAL PREPARATIONS CONTAINING SUCH COMPOUNDS

This is a continuation of application Ser. No. 061,097 filed on July 26, 1979, U.S. Pat. No. 4,297,365.

The invention relates to novel benzimidazoles, especially benzimidazolecarbamates of the formula I

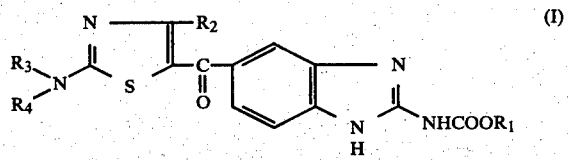

in which $R_1$ is a substituted or unsubstituted hydrocarbon radical of aliphatic, cycloaliphatic, cycloaliphaticaliphatic or aromatic character, $R_2$ is hydrogen or a substituted or unsubstituted hydrocarbon radical of aliphatic character and $R_3$ and $R_4$ are hydrogen or a substituted or unsubstituted hydrocarbon radical of aliphatic, cycloaliphatic or aromatic character, or taken together are a substituted or unsubstituted divalent hydrocarbon radical of aliphatic character, in which the carbon atoms of the chain can be interrupted by a hetero-atom, their tautomeric compounds and salts and processes for their preparation, the compounds of the formula I and their salts as pharmacologically active compounds, pharmaceutical preparations containing such compounds and the use of the novel compounds as pharmacologically active substances and for the production of pharmaceutical preparations.

In this specification the term "lower" used to qualify radicals and compounds denotes that these contain preferably not more than 7 and in particular not more than 4 carbon atoms.

An aliphatic hydrocarbon radical $R_1$, $R_2$ or $R_3$, which can be substituted, is in particular an alkyl radical or an alkenyl or alkynyl radical, especially a straight-chain or branched lower alkyl radical or lower alkenyl or lower alkynyl radical. Substituents of aliphatic hydrocarbon radicals are, for example, free, esterified or etherified hydroxyl groups, such as lower alkanoyloxy, lower alkoxy or lower alkenyloxy groups, or halogen atoms, and also free or esterified carboxyl groups, such as lower alkoxycarbonyl.

Lower alkyl groups are, for example, preferably methyl groups and also ethyl, n-propyl, isopropyl, n-butyl, isobutyl, sec.-butyl, tert.-butyl, n-pentyl, isopentyl, neopentyl, n-hexyl, isohexyl or n-heptyl groups; lower alkenyl groups are, for example, the allyl group or the 2-methylallyl group, and lower alkynyl groups are preferably propargyl groups. Substituted lower alkyl groups are, for example, the trifluoromethyl group or a free or esterified carboxymethyl group, for example a lower alkoxycarbonylmethyl group, for example a methoxycarbonylmethyl group.

Lower alkoxy is, for example, methoxy, ethoxy, n-propoxy, isopropoxy, n-butoxy or n-pentyloxy and lower alkenyloxy is, for example, vinyloxy or allyloxy.

Halogen atoms are in particular fluorine, chlorine or bromine atoms, but can also be iodine atoms.

A cycloaliphatic hydrocarbons radical is in particular a monocyclic or polycyclic cycloalkyl radical having, for example, not more than 12 and preferably 3 to 10 ring carbon atoms.

A cycloalkyl group is, for example, a cyclopropyl, cyclobutyl, cyclopentyl, cyclohexyl, cycloheptyl or adamantyl group.

In a cycloaliphatic-aliphatic hydrocarbon radical $R_1$, the cycloaliphatic radical is, for example, as defined above and is preferably a cycloalkyl radical. The aliphatic moiety of such a cycloaliphatic-aliphatic radical is, for example, an alkylene radical, preferably a lower alkylene radical.

A cycloalkyl-lower alkyl group is, for example, a cyclopropylmethyl, cyclopropyl-1,1- or -1,2-ethyl, cyclopentylmethyl, cyclopentyl-1,1- or -1,2-ethyl or cyclopentyl-1,2- or -1,3-propyl, cyclohexylmethyl, cyclohexyl-1,1- or -1,2-ethyl or cyclohexyl-1,2- or -1,3-propyl or cycloheptylmethyl radical.

As hydrocarbon radicals of aromatic character, the substituents $R_1$, $R_3$ and $R_4$ can be a carbocyclic aromatic radical or a heterocyclic radical of aromatic character. A carbocyclic aromatic radical is a monocyclic or bicyclic radical, for example naphthyl, but especially phenyl, which can be substituted by one, two or more identical or different substituents. Such substituents are, for example, hydrocarbon radicals, such as lower aliphatic hydrocarbons radicals, for example lower alkyl, free or functionally modified hydroxyl or mercapto, such as etherified hydroxyl, for example lower alkoxy, lower alkenyloxy or lower alkylenedioxy, and also lower alkylthio, or halogen, trifluoromethyl, nitro, amino, including substituted amino, for example lower alkylamino or di-lower alkylamino, and free or functionally modified carboxyl, such as esterified carboxyl, for example lower alkoxycarbonyl.

A heterocyclic radical of aromatic character is in particular a monocyclic or also a bicylic, monoazacyclic, monooxacyclic or monothiacyclic radical of aromatic character, which, for example, can be substituted in the same way as the aromatic hydrocarbon radical mentioned above. The heterocyclic radical can be bonded in any position and is, for example, pyrrolyl, pyridyl, quinolyl, furyl or thienyl.

Pyrrolyl is, for example, pyrrol-2-yl or pyrrol-3-yl, pyridyl is, for example, 2-, 3- or 4-pyridyl, quinolyl is, for example, 2-, 3- or 4-quinolyl, furyl is, for example, 2- or 3-furyl and thienyl is, for example, 2- or 3-thienyl.

Substituents on the nitrogen atom are, for example, lower alkyl radicals, for example methyl, ethyl, n-propyl, isopropyl, n-butyl, n-pentyl or n-hexyl, or aromatic hydrocarbon radicals, for example a substituted or unsubstituted phenyl radical, as already described above.

The two substituents $R_3$ and $R_4$ taken together can also be a substituted or unsubstituted divalent aliphatic hydrocarbon radical having 4-7 carbon atoms in the chain.

The group $-NR_3R_4$ in the 2-position of the thiazole ring is, for example, lower alkylamino or di-lower alkylamino, for example methylamino, dimethylamino, ethylamino, diethylamino, n-propylamino, di-n-propylamino, isopropylamino, di-isopropylamino or di-n-butylamino. This group is, however, also lower alkyleneamino, in which the lower alkylene chain can be interrupted, for example by a hetero-atom, for example oxygen, sulfur or substituted or unsubstituted nitrogen, and is, for example, lower alkyleneamino, for example, pyrrolidino, 2,5-dimethylpyrrolidino, piperidino, 2-methylpiperidino, hexahydroazepino or octahydroazocino, oxa-lower alkyleneamino, for example morpholino, thia-lower alkyleneamino, for example thiomorpholino, and aza-lower alkyleneamino, for example piperazino or N-methyl- or N-phenyl-piperazino.

The novel compounds have valuable pharmacological properties. They make possible an advance in the control of parasitic helminths, i.e. in the treatment of parasitic infections by helminths. The term "helminths" relates to nematodes, cestodes and trematodes, ie. to worms which in the main infest the gastrointestinal tract, the liver and also other organs. The compounds are in the main particularly suitable for controlling parasitic nematodes, for example Ascaridae, Trichostrongylidae, Strongylidae and Ancylostomatidae (hookworm), and cestodes, for example Taeniidae and Anoplocephalidae, and trematodes, for example Fasciolodae.

When administered orally in doses of 10 to 100 mg/kg or parenterally in doses of 5 to 25 mg/kg to animals, for example to hamsters which have been experimentally infested with Necator americanus or Ancylostoma ceylanicum or to dogs which have become naturally infected with Ancylostoma caninum, the novel compounds eliminate the corresponding worms.

The novel compounds mentioned are suitable as agents having an anthelmintic action, especially as agents against hookworm.

The invention relates in particular to compounds of the formula I in which $R_1$ is lower alkyl, cycloalkyl or phenyl, $R_2$ is hydrogen or lower alkyl and $R_3$ and $R_4$ are each hydrogen, lower alkyl, lower alkenyl, cycloalkyl or phenyl, which is unsubstituted or substituted, for example by lower alkyl, lower alkoxy or halogen, or $R_3$ and $R_4$ taken together are a lower alkylene chain, which can be interrupted by an oxygen or sulfur atom or by a nitrogen atom which can be substituted, for example by lower alkyl, and their tautomeric compounds and salts.

The invention relates especially to those compounds of the formula I in which $R_1$ is lower alkyl, $R_2$ is hydrogen or lower alkyl and $R_3$ and $R_4$ are each hydrogen, lower alkyl, lower alkenyl, cycloalkyl or phenyl, or $R_3$ and $R_4$ taken together with the adjacent nitrogen atom are lower alkyleneamino, for example pyrrolidino or piperidino, and their tautomeric compounds and salts, especially the pharmaceutically usable non-toxic salts.

Compounds of the formula I which are of particular interest in this invention are those in which $R_1$ is lower alkyl, for example methyl or ethyl, $R_2$ is lower alkyl, for example methyl or ethyl, $R_3$ is hydrogen and $R_4$ is lower alkyl, for example methyl, ethyl, n-propyl, isopropyl, n-butyl or isobutyl, and their tautomeric compounds and salts, especially pharmaceutically usable, non-toxic salts.

The compounds of the formula I described in the examples, and their salts, especially their pharmaceutically usable, non-toxic salts, are particularly preferred.

The novel benzimidazoles of the formula I are obtained by methods known per se.

Thus, for example, the novel benzimidazoles of the formula I can be obtained by reacting a substituted o-phenylenediamine derivative of the formula II

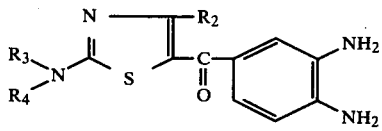

in which $R_2$, $R_3$ and $R_4$ are as defined under formula I, or a salt thereof, with a compound of the formula III

in which $R_x$ is hydrogen or the $COOR_1$ group and $R_y$ is the cyano group, or $R_x$ and $R_y$ taken together are a disubstituted methylene group of the formula

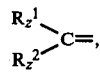

in which $R_z^1$ is an alkylthio or arylthio group and $R_z^2$ is an alkylthio or arylthio group, an amino group or the $NHCOOR_1$ group, and, if desired, carrying out additional process steps.

The compounds of the formula III which are used in the process described are, for example, compounds of the type having the formulae $NC-NH-COOR_1$, $NC-N(COOR_1)_2$,

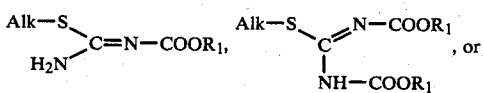

Compounds of the formula III are obtained by acylating the corresponding cyanamides or isothiourea compounds with compounds which donate the group $COOR_1$. For example, monoacylated S-lower alkyl-isothioureas or diacylated S-lower alkyl-isothioureas in which the acyl radical is a $COOR_1$ group can be obtained by reacting S-lower alkyl-isothioureas with one or two equivalents of a suitable halogenoformate Hal-$COOR_1$ in a cooled aqueous or alcoholic medium, if necessary in the presence of a base. If desired, the corresponding reaction mixture can also be obtained in situ in that reaction medium in which the subsequent reaction with the corresponding thiazolyl-o-phenylenediamine derivative or salt takes place. Thus, for example, either monosubstituted or disubstituted derivatives of the formulae

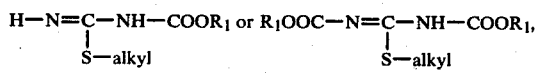

in which $R_1$ is as defined above, are obtained by treating a S-lower alkyl-isothiourea with a compound of the formula Cl-$COOR_1$.

In a typical reaction for the process described for the preparation of compounds of the formula I, hydrohalide salts of o-phenylenediamine compounds of the formula II are reacted with one equivalent or with two equivalents of a monoacyl- or S-diacyl-lower alkyl-isothiourea compound, in which acyl is a $COOR_1$ group, in aqueous solution in the presence of an acid-binding agent, for example sodium acetate, at a temperature of 30° to 200° C. and a pH value of 4-6. The reaction of an alkyl [bis-(alkylthio or arylthio)-methylene]-aminoformate with a compound of the formula II takes place with heating in an inert solvent, for example tetrahydrofuran or dioxan.

In a further process variant, o-phenylenediamine derivatives of the formula II can be reacted with a mononoor bis-(N-$R_1$OOC)-cyanamide in an aqueous or alcoholic solution at a temperature of 30° to 200° C. and a pH value of 4–9.

According to a second process, compounds of the formula I are obtained by reacting a compound of the formula IV

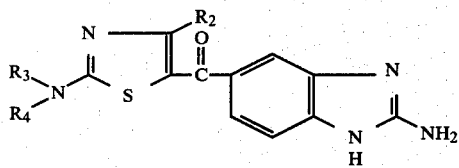

in which $R_2$ is as defined above and $R_3$ and $R_4$ have the meanings defined above with the exception of hydrogen, with a compound of the formula V

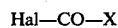

in which X is a halogen atom or the group -$OR_1$, and, if appropriate, if a compound of the formula V is used in which X is halogen, replacing the halogen atom in the resulting halogenocarbonylamino compound of the formula VI

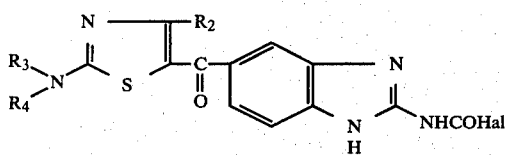

by the group -$OR_1$, and, if desired, carrying out additional process steps.

The compounds of the formula V used for the reaction described are preferably alkyl halogenoformates, especially lower alkyl chloroformates. The reaction of the aminobenzimidazole derivative of the formula IV with a lower alkyl chloroformate takes place under the conditions customary for this reaction, i.e. in the presence of a suitable acid-binding agent, for example of an organic or inorganic base, and of a suitable solvent. The reaction is preferably carried out with heating at a temperature of from 50° C. to the reflux temperature.

However, the reaction described can also be carried out in two steps using a dihalide of carbonic acid, preferably using the dichloride (phosgene), and subsequently reacting the product with an alcohol to give the carbamate.

According to a third process, compounds of the general formula I are obtained by treating compounds of the general formula VII

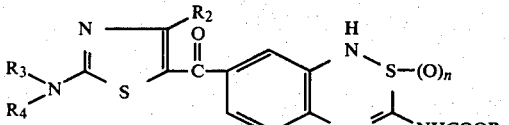

in which $R_1$, $R_2$, $R_3$ and $R_4$ are as defined above and n is the symbol 0 or the integer 1, with an acid and, if desired, carrying out additional process steps.

The acid used is preferably a mineral acid, for example sulfuric acid or a hydrogen halide acid, for example hydrochloric acid.

The conversion of a compound of the formula VII by treatment with a mineral acid is preferably effected at elevated temperature, i.e. at about 50° C. up to the reflux temperature, and, depending on the value of the symbol n, the benzimidazole ring is formed by the detaching of a sulfur atom or of sulfur monoxide.

Compounds of the general formula I are also obtained by a further process, by cyclising a o-aminothioallophanate of the formula VIII

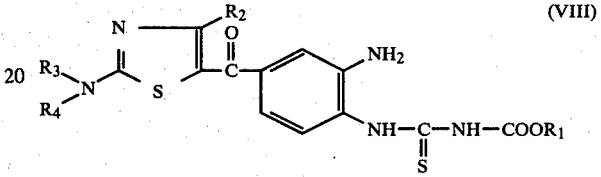

in which $R_1$, $R_2$, $R_3$ and $R_4$ are as defined under formula I, in the presence of an acid, preferably a mineral acid, and, if desired, carrying out additional process steps.

The cyclisation of an o-aminothioallophanate of the general formula VIII to a benzimidazole derivative of the formula I is, if necessary, carried out at elevated temperature, for example by heating under reflux in an aqueous mineral acid. The aqueous mineral acid used is, for example, dilute hydrochloric acid.

The compounds, according to the invention, of the formula I in which one of the radicals $R_3$ and $R_4$ is hydrogen and the other has a meaning defined for $R_3$ or $R_4$ other than hydrogen can be prepared by a further process, by detaching the amino protective group in compounds of the formula

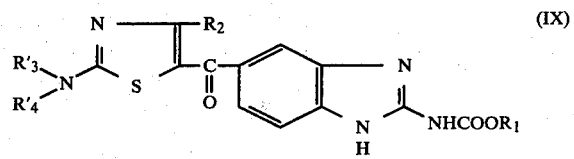

in which $R_1$ and $R_2$ are as defined above and one of the two substituents $R_3'$ and $R_4'$ is hydrogen or has the meaning defined for $R_3$ or $R_4$ and the other is an amino protective group, and, if desired, carrying out additional process steps.

Protective groups $R_3'$ and $R_4'$ can be detached, for example, by means of solvolysis or by reduction. Such groups are in particular acyl radicals, especially of carbonic acid half-esters.

Amino protective groups $R_3'$ and $R_4'$ are, for example, 2-halogeno-lower alkoxycarbonyl groups, for example the 2,2,2-trichloroethoxycarbonyl group or the 2-iodoethoxycarbonyl group, which can be detached by reduction by treatment with a metal or a corresponding metal salt, for example by treatment with zinc in aqueous acetic acid or by treatment with a chromium-II salt, for example chromium-II chloride or chromium-II acetate.

Further amino protective groups are suitable lower alkoxycarbonyl groups, such as tert.-butoxycarbonyl, which are detachable by acidolysis, for example by treatment with trifluoroacetic acid.

A further detachable amino protective group is an ethoxycarbonyl group which in the β-position carries a silyl group substituted by three hydrocarbon radicals, such as a triphenylsilyl, dimethyl-butyl-silyl or, in particular, a trimethylsilyl group. A β-(tri-lower alkylsilyl-)ethoxycarbonyl group of this type together with the amino group to be protected forms a corresponding β-tri-lower alkylsilyl-ethoxycarbonylamino group, which can be detached under mild conditions by the action of fluoride ions. Reagents which can be used as fluoride ion donors are, for example, fluorides of quaternary organic bases, such as tetraethylammonium fluoride.

a further group suitable as an amino protective group of this type is a benzyloxycarbonyl group, which can be substituted by a nitro group, for example a p-nitrobenzyloxycarbonyl group, which can be detached by means of hydrogen in the presence of palladium-on-charcoal as the catalyst or, if it is suitably substituted by nitro, by treatment with zinc and acetic acid.

A condition which must be observed is that only those amino protective groups which are selectively detachable whilst retaining the carbamate radical —NHCOOR$_1$ are suitable as amino protective groups R$_3'$ and R$_4'$. Furthermore, the keto group present should not be reduced.

The processes described can be carried out in the conventional manner at room temperature, with cooling or warming, under normal pressure or elevated pressure and, if necessary, in the presence or absence of a diluent, catalyst or condensing agent. If necessary, the reactions can also be carried out in the atmosphere of an inert gas, for example nitrogen.

In resulting compounds, substituents can be introduced, modified or detached, within the scope of the definition of the end products.

Depending on the process conditions and the starting materials, the end products are obtained in the free form or in the form of their salts, especially acid addition salts, which is also included in the invention. The acid addition salts of the novel compounds can be converted to the free compound in a manner known per se, for example with basic agents, such as alkalis or ion exchangers. On the other hand, the resulting free bases can form salts with organic or inorganic acids. Acids used to prepare acid addition salts are in particular those which are suitable for forming therapeutically usable salts. Examples of such acids are: hydrogen halide acids, sulfuric acids, phosphoric acids, nitric acid, perchloric acid and aliphatic, alicyclic, aromatic or heterocyclic carboxylic or sulfonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicylic acid, embonic acid, methanesulfonic acid, ethanesulfonic acid, hydroxyethanesulfonic acid or ethylenesulfonic acid; a halogenobenzenesulfonic acid, toluenesulfonic acid, naphthalenesulfonic acid or sulfanilic acid; and methionine, tryptophan, lysine or arginine.

These or other salts of the novel compounds, for example the picrates, can also be used to purify the resulting free bases, by converting the free bases to salts, separating these off and liberating the bases again from the salts. Because of the close relationship between the novel compounds in the free form and in the form of their salts, what is stated in this specification in respect of the free compounds also applies by analogy to the corresponding salts.

The invention also relates to those embodiments of a process in which a process is discontinued at any stage or in which a compound obtainable as an intermediate at any stage is used as the starting material and the missing process steps are carried out, or a starting material is formed under the reaction conditions or, if desired, is used in the form of a salt. The invention also includes novel intermediates resulting therefrom.

The starting materials are known or, if they are novel, can be prepared by methods known per se.

Starting compounds of the formula II can be prepared by a sequence of known reaction steps using a 4-halogeno-3-nitro-acetophenone as the starting material. Bromination of the active methylene group of the acetyl radical yields a compound of the formula X, which on reaction with a thiourea derivative of the formula XI

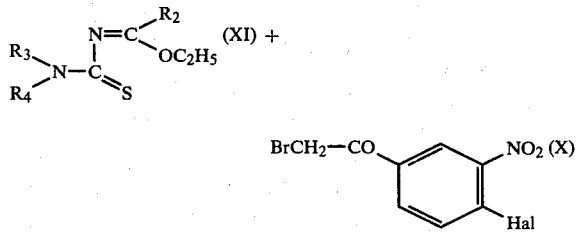

yields a compound of the formula XII

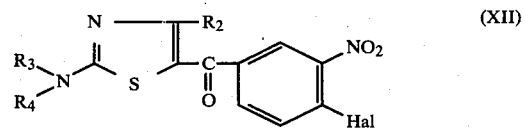

in which R$_2$, R$_3$ and R$_4$ are as defined under formula I and Hal is a halogen atom.

The reaction of a compound of the formula XII obtained in this way with aqueous or alcoholic ammonia, if necessary with the use of pressure and a catalyst, for example ethylene glycol, yields a nitroaniline of the formula XIII

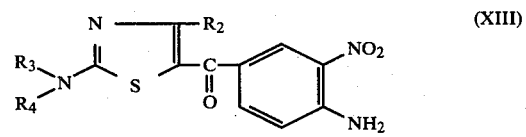

from which, in turn, the o-phenylenediamine derivative of the formula II, which is used as the starting material in the first process, is obtained by reduction using a suitable reducing agent.

The reduction of the aromatic nitro compound of the formula XIII is effected in a manner known per se, by hydrogenation in the presence of a palladium-on-charcoal catalyst in a suitable solvent. This reduction can also be carried out by a chemical route, for example using metals, for example zinc, in the presence of acids, preferably mineral acids, for example hydrochloric acid, or alkanecarboxylic acids, for example acetic acid or trifluoroacetic acid. In specific cases glacial acetic acid can also be used.

The bis-(alkylthio- or -arylthio)-methyleneaminoformates of the formula

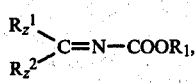

which are used in the first process and in which $R_z^1$ and $R_z^2$ are an alkylthio or arylthio group are prepared by reacting a bis-(alkylthio- or -arylthio)-methyleneamine with a halogenoformate, especially with a chloroformate. The monoacylated or bis-acylated S-lower alkyl-isothioureas of the formula

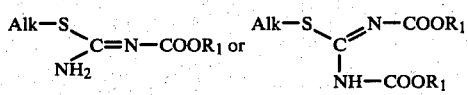

which are also used in the first process and have already been mentioned briefly above are prepared by acylating S-lower alkyl-isothioureas with a chloroformate in a suitable solvent, for example water, and then treating the product with a base, for example an aqueous alkali. The starting compounds used for this reaction are prepared and at the same time used in situ for the reaction.

The cyanamides of the formula $NC-NH-COOR_1$ mentioned in the process can be obtained by reacting cyanamide with a suitable halogenoformate, for example a chloroformate.

The starting compounds of the formula IV used in the second process can be obtained by reacting a cyanogen halide, especially cyanogen bromide, with an o-phenylenediamine derivative of the formula II, as described in the literature [J. Am. Chem. Soc. 69, 2459 (1947)].

The starting compounds of the formula VII which are used in the third process are obtained, in turn, by treating o-aminothioallophanates of the formula VIII with an oxidising agent, for example a halogen gas, especially bromine. Subsequent treatment with a peracid yields compounds of the formula VII in which the symbol n is an integer 1.

The o-amino-thioallophanate of the formula VIII which is used in the fourth process is prepared by reacting an o-amino-phenylenediamine compound of the formula II with an isothiocyanic acid derivative of the formula $SCN-COOR_1$. The reaction is preferably carried out in a solvent which releases protons, for example an acid, if necessary with the application of heat.

The starting compounds of the formula IX used in the fifth process are prepared by reacting a modified o-phenylenediamine compound of the formula IIa

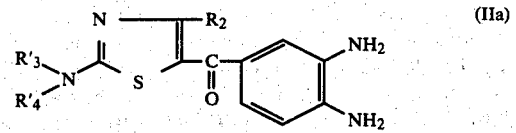

in which one of the substituents $R_3'$ and $R_4'$ is hydrogen and the other is a detachable amino protective group, with a compound of the formula III

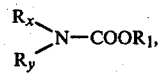

in which $R_1$, $R_x$ and $R_y$ are as defined above. Starting compounds of the formula IIa are prepared analogously to compounds of the formula II.

The invention also comprises therapeutic compositions of matter which consist of an anthelmintically active amount of the compounds of the general formula I, or an acid addition salt, and a pharmacologically acceptable solid carrier or liquid diluents.

The pharmaceutical preparations according to the invention contain at least one compound of the general formula I, or a salt thereof, as the active ingredient, together with a conventional pharmaceutical carrier. The nature of the carriers largely depends on the field of application. The pharmaceutical compositions of matter according to the invention, which contain compounds of the formula I as active ingredients, can be administered orally, parenterally or rectally.

Preparations suitable for the oral treatment of parasitic infections of the gastrointestinal tract, of the liver and of other organs are, in particular, solid dosage unit forms, such as tablets, sugar-coated tablets and capsules, which preferably contain between 10 and 90% of an active ingredient of the general formula I, or of a salt, in order to enable daily doses of between 1.5 and 100 mg/kg to be administered to warm-blooded animals. To prepare tablets and sugar-coated tablet cores, the compounds of the general formula I are combined with solid, pulverulent carriers, such as lactose, sucrose, sorbitol, maize starch, potato starch or amylopectin, cellulose derivatives or gelatine, preferably with the addition of lubricants, such as magnesium stearate or calcium stearate, or polyethylene glycols of suitable molecular weight. Sugar-coated tablet cores are subsequently coated with, for example, concentrated sugar solutions, which can additionally contain, for example, gum arabic, talc and/or titanium dioxide, or with a lacquer which is dissolved in readily volatile organic solvents or solvent mixtures. Colorants can be added to these coatings, for example to distinguish different doses of active ingredient. Soft gelatine capsules and other sealed capsules consist, for example, of a mixture of gelatine and glycerin and can contain, for example, mixtures of a compound of the formula I with polyethylene glycol. Dry-filled capsules contain, for example, granules of an active ingredient with solid, pulverulent carriers, for example lactose, sucrose, sorbitol or mannitol; starches, such as potato starch, maize starch or amylopectin, cellulose derivatives and gelatine as well as magnesium stearate or stearic acid.

Suitable dosage unit forms for rectal administration are, for example, suppositories, which consist of a combination of an active ingredient with a suppository base based on natural or synthetic triglycerides (for example cacao butter), polyethylene glycols or suitable higher fatty alcohols, and gelatine rectal capsules which contain a combination of the active ingredient with polyethylene glycols.

Ampoule solutions for parenteral, and in particular intramuscular or intravenous, administration contain a compound of the formula I or a salt thereof in a concentration of preferably 0.5 to 5% in the form of an aqueous dispersion, prepared with the aid of conventional solubilising agents and/or emulsifiers and also, if necessary, stabilisers, or preferably contain an aqueous solution of a pharmaceutically acceptable, water-soluble acid addition salt of a compound of the general formula I.

For liquids to be taken orally, such as syrups and elixirs, the concentration of the active ingredient is so chosen that an individual dose can be measured out easily, for example as the contents of a teaspoon or of a measuring spoon, for example a 5 ml measuring spoon, or as a multiple of these volumes.

The following examples (a) to (e) will serve to illustrate the preparation of some typical administration forms, but in no way represent the only embodiments of such forms.

(a) 250.0 g of active ingredient are mixed with 550.0 g of lactose and 292.0 g of potato starch and the mixture is moistened with an alcoholic solution of 8 g of gelatine and granulated through a sieve. After drying, 60.0 g of talc, 10.0 g of magnesium stearate and 20.0 g of colloidal silica are mixed in and the mixture is compressed to 10,000 tablets each weighing 125 mg and containing 25 mg of active ingredient; if desired, the tablets can be provided with a breaking notch for finer adjustment of the dosage.

(b) Granules are prepared from 100.0 g of active ingredient, 379.0 g of lactose and an alcoholic solution of 6.0 g of gelatine and, after drying, these are mixed with 10.0 g of colloidal silica, 40.0 g of talc, 60.0 g of potato starch and 5.0 g of magnesium stearate and the mixture is compressed to 10,000 sugar-coated tablet cores. These are then coated with a concentrated syrup of 533.5 g of crystalline sucrose, 20.0 g of Shellack 75.0 g of gum arabic, 250.0 g of talc, 20.0 g of colloidal silica and 1.5 g of a dye and dried. The resulting sugar-coated tablets each weigh 150 mg and each contain 10 mg of active ingredient.

(c) 25.0 g of active ingredient and 1,975 g of finely ground suppository base (for example cacao butter) are mixed thoroughly and the mixture is then melted. 1,000 2.0 g suppositories are cast from the melt, which is kept homogeneous by stirring. Each suppository contains 25 mg of active ingredient.

(d) To prepare a syrup containing 0.25% of active ingredient, 1.5 liters of glycerin, 42 g of methyl p-hydroxybenzoate, 18 g of n-propyl p-hydroxybenzoate and, with gentle warming, 25.0 g of active ingredient are dissolved in 3 liters of distilled water, 4 liters of 70% sorbitol solution, 1,000 g of crystalline sucrose, 350 g of glucose and an aroma substance, for example 250 g of "Orange Peel Soluble Fluid" from Eli Lilly and Co., Indianapolis, or 5 g of natural lemon aroma and 5 g of "half and half" essence, both from Haarmann and Reimer, Holzminden, Germany, are added, the resulting solution is filtered and the filtrate is made up to 10 liters with distilled water.

(e) To prepare a drip solution containing 1.5% of active ingredient, 150.0 g of active ingredient and 30 g of sodium cyclamate are dissolved in a mixture of 4 liters of ethanol (96%) and 1 liter of propylene glycol. A mixture of 3.5 liters of 70% sorbitol solution and 1 liter of water is prepared separately and added to the above solution of active ingredient. An aroma substance, for example 5 g of cough sweet aroma or 30 g of Grapefruit Essence, both from Haarmann and Reimer, Holzminden, Germany, is then added and the whole is mixed well and filtered and the filtrate is made up to 10 liters with distilled water.

The following examples illustrate the preparation of the novel compounds of the general formula I without, however, restricting the scope of the invention in any way. The temperatures are in degrees centigrade.

EXAMPLE 1

The "reagent" is prepared in situ as follows: A mixture of 4.2 g of 5-methyl-isothiourea sulfate and 5 ml of water is cooled to 0°–2° with stirring and is treated at this temperature with 3.2 g of ethyl chloroformate, which is added dropwise in the course of 10 minutes. The reaction mixture is stirred for 15 minutes at the indicated temperature and then treated with 5–6 ml of a 25% aqueous sodium hydroxide solution until a pH value of 7.5–8 is obtained, the temperature being kept below 5°. The mixture is stirred at this temperature for 15 minutes and then treated at 0°–2° with 2 ml of glacial acetic acid, which is added dropwise, the pH value being brought to 5–5.5.

A solution of 4 g of 1,2-diamino-4-(4-methyl-2-methylamino-5-thiazolyl)-benzene in 150 ml of methanol is added all at once to the above reagent mixture. The reaction mixture is refluxed for 2 hours, with stirring, cooled to 0° and filtered and the material on the filter is washed with 50% aqueous methanol. The resulting solid material is purified by dissolving in 2-normal hydrochloric acid and precipitating with ammonia and finally is washed with water, yielding 2-carboethoxyamino-5(6)-(4-methyl-2-methylamino-5-thiazoloyl)-benzimidazole of the formula

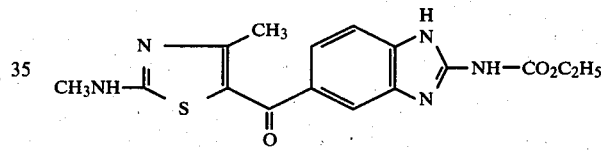

which melts at 280°–285° with decomposition.

The starting material for the above synthesis is prepared as follows: A mixture of 17 g of ethyl imidoacetate and 14 g of methyl isothiocyanate is warmed on a water bath for 2 hours and cooled and the adduct is used as such in the next process step.

A solution of 30 g of the above adduct in 300 ml of isopropanol is refluxed with 33 g of 4-chloro-3-nitrophenacyl bromide. After cooling, the solid material is filtered off and rendered basic with sodium hydroxide, the mixture is filtered and the material on the filter is washed with water and recrystallised from aqueous acetic acid, yielding 4-chloro-3-nitro-1-(4-methyl-2-methylamino-5-thiazoloyl)-benzene, which melts at 220°–232°.

A mixture of 4 g of the above chlorine compound and 40 ml of an alcoholic ammonia solution, which contains 0.2 ml of ethylene glycol, is heated in a bomb tube for 16 hours at 130°, cooled and filtered and the residue is washed with water. The solid material is recrystallised from aqueous acetic acid, yielding 1-amino-2-nitro-4-(4-methyl-2-methylamino-5-thiazoloyl)-benzene, which melts at 260°–261° with decomposition.

A mixture of 40 g of stannous chloride dihydrate in 150 ml of acetic acid is saturated with dry hydrogen chloride gas and the above nitro compound is then added in small portions, with stirring. The solution is stirred at 30° for a further 2 hours and the solvent is then evaporated off in vacuo. The residue is rendered basic with 50% aqueous potassium hydroxide solution and the mixture is filtered. The residue is extracted with hot methanol, the solvent is evaporated off and the residue is digested with isopropanol. The product is recrystalised from methanol, yielding 1,2-diamino-4-(4-methyl-2-methylamino-5-thiazoloyl)-benzene in the form of a hygroscopic solid material which melts at 115°–125°.

EXAMPLE 2

The reagent is prepared in situ analogously to Example 1, using 4.5 g of S-methyl-isothiourea sulfate and 3.5 g of ethyl chloroformate as the starting materials. A solution of 4.5 g of 1,2-diamino-4-(4-methyl-2-ethylamino-5-thiazoloyl)-benzene in 100 ml of methanol is added to the resulting solution and the mixture is refluxed for 2 hours. The reaction mixture is left to stand overnight at 30° and the resulting solid material is filtered off, washed with hot methanol and purified by dissolving in 2-normal hydrochloric acid and precipitating with ammonia, yielding 2-carboethoxyamino-5(6)-(4-methyl-2-methylamino-5-thiazoloyl)-benzimidazole, which melts at 250°–255° (decomposition).

The starting material is prepared as follows: A mixture of 20 g of ethyl imidoacetate and 20 g of ethyl isothiocyanate is warmed for 2 hours, with stirring. A mixture of 35 g of the resulting crude adduct and 56 g of 4-chloro-3-nitro-phenacyl bromide in 300 ml of isopropanol is refluxed for 2 hours and worked up analogously to Example 1, yielding 4-chloro-3-nitro-1-(4-methyl-2-ethylamino-5-thiazoloyl)-benzene, which melts at 195°.

A mixture of 4 g of the above chlorine compound and 0.4 g of ethylene glycol in 40 ml of alcoholic ammonia solution is heated at 100° in a bomb tube for 16 hours, cooled and filtered and the residue is washed with water and recrystallised from aqueous acetic acid, yielding 1-amino-2-nitro-4-(4-methyl-2-ethylamino-5-thiazoloyl)-benzene, which melts at 220°–225° (decomposition).

9 g of the above nitro compound are reduced with 45 g of stannous chloride in 150 ml of acetic acid and the reaction mixture is worked up analogously to Example 1, yielding crude 1,2-diamino-4-(4-methyl-2-ethylamino-5-thiazoloyl)-benzene, which melts at 185°–225°.

EXAMPLE 3

The reagent is prepared in situ analogously to Example 1, using 8.5 g of S-methyl-isothiourea sulfate and 6.5 g of ethyl chloroformate as the starting materials. A solution of 9 g of 1,2-diamino-4-(4-methyl-2-n-butylamino-5-thiazoloyl)-benzene in 100 ml of methanol is added to the solution and the mixture is refluxed for 4 hours. After cooling, the precipitate is filtered off, washed with hot methanol and purified by dissolving in 2-normal hydrochloric acid and precipitating with ammonia, yielding 2-carboethoxyamino-5(6)-(4-methyl-2-n-butylamino-5-thiazoloyl)-benzimidazole hemihydrate, which melts at 208°–212° (decomposition). The anhydrous product is prepared by washing with hot methanol and drying. Melting point 229°–233°.

The base is converted to the hydrochloride by treating with ethanolic hydrogen chloride and evaporating. A solution of 4.7 g of this hydrochloride in water is treated with a solution of 4.3 g of disodium pamoate in 20 ml of water. The resulting precipitate is filtered off, washed with water and dried, yielding the corresponding pamoate, which melts at 240°–245° (decomposition).

The starting material is prepared as follows: 15 g of ethyl imidoacetate are reacted with 20 g of n-butyl isothiocyanate at 60° for 2 hours. A mixture of 10 g of the resulting adduct and 15 g of 4-chloro-3-nitro-phenacyl bromide in 100 ml of isopropanol is refluxed for 2 hours and evaporated, water is added to the residue and the resulting mixture is worked up analogously to Example 1, yielding 4-chloro-3-nitro-1-(4-methyl-2-n-butylamino-5-thiazoloyl)-benzene, which melts at 125°–128°.

The same compound is also prepared as follows: 11.5 g of n-butyl isothiocyanate are added to 11.4 g of N,N-diethyl-acetamidine, whereupon the mixture becomes exothermic. The mixture is left to stand for 1 hour at 60° and the resulting adduct is used in the following experiment. A mixture of 22.9 g of the crude product and 27.9 g of 4-chloro-3-nitro-phenacyl bromide in 200 ml of isopropanol is refluxed for 2 hours. The solution is worked up as described above, yielding 4-chloro-3-nitro-1-(4-methyl-2-n-butylamino-5-thiazoloyl)-benzene.

A solution of 30 g of the last-mentioned compound in 300 ml of alcoholic ammonia is heated at 100° in a bomb tube for 20 hours, cooled and filtered and the material on the filter is washed with water, affording 1-amino-2-nitro-4-(4-methyl-2-n-butylamino-5-thiazoloyl)-benzene, which melts at 200°–205°.

50 g of the above nitro compound are added in portions in the course of 20–30 minutes to a solution of 250 g of stannous chloride dihydrate in 500 ml of concentrated hydrochloric acid, with stirring. The solution is stirred overnight at 30° and then evaporated in vacuo. The residue is dissolved in a minimal amount of water and the solution is cooled and rendered basic with potassium hydroxide. The resulting precipitate is filtered off, washed with water and extracted with hot ethyl acetate. The extract is concentrated, treated with ether, cooled and filtered, yielding 1,2-diamino-4-(4-methyl-2-n-butylamino-5-thiazoloyl)-benzene, which melts at 127°–130°.

EXAMPLE 4

7 g of 1-amino-2-nitro-4-(4-methyl-2-isobutylamino-5-thiazoloyl)-benzene are reduced with 40 g of stannous chloride in 150 ml of acetic acid analogously to Example 1. Oily 1,2-diamino-4-(4-methyl-2-isobutylamino-5-thiazoloyl)-benzene is obtained and this is used in the following step.

A solution of 3 g of the above diamine in 30 ml of methanol is added to a reagent solution which has been prepared beforehand (analogously to Example 1) from 2.8 g of S-methyl-isothiourea sulfate and 2.2 of ethyl chloroformate. The solution is stirred and refluxed for 3 hours. The methanol is distilled off and replaced by 50 ml of water and the reaction mixture is refluxed for 2 hours. The solution is cooled and filtered and the residue is washed with water and recrystallised from methanol, yielding 2-carboethoxyamino-5(6)-(4-methyl-2-isobutylamino-5-thiazoloyl)-benzimidazole hemihydrate, which melts at 178°–180° (decomposition).

The starting material is prepared as follows: A mixture of 8.7 g of ethyl imidoacetate and 11.5 g of isobutyl isothiocyanate is kept at 60° for 4 hours. A mixture of 20 g of the resulting crude adduct and 26.8 g of 4-chloro-3-nitro-phenacyl bromide in 150 ml of isopropanol is refluxed for 2 hours and the solvent is evaporated. The residue is rendered basic with sodium bicarbonate solution and extracted with ethyl acetate. The extract is dried and evaporated. The residue is recrystallised from a mixture of ethyl acetate and hexane, yielding 4-chloro-3-nitro-1-(4-methyl-2-isobutylamino-5-thiazoloyl)-benzene, which melts at 138°–142°.

A solution of 9 g of the above chlorine compound in 150 ml of ethanol ammonia is heated at 120° in a bomb tube for 12 hours and cooled and the solvent is evaporated off. Water is added to the residue, the mixture is filtered and the material on the filter is dried, yielding 1-amino-2-nitro-4-(4-methyl-2-isobutylamino-5-thiazoloyl)-benzene, which melts at 210°–215°.

EXAMPLE 5

5.5 g of 1-amino-2-nitro-4-(4-methyl-2-n-pentylamino-5-thiazolyl)-benzene are reduced with 25 g of stannous chloride in 100 ml of acetic acid, analogously to Example 1. The resulting gum-like diamine is employed in the subsequent cyclisation.

A solution of 3.8 g of the above diamine in 50 ml of methanol is added to a reagent solution which has been prepared beforehand (analogously to Example 1) from 3.4 g of S-methyl-isothiourea sulfate and 2.7 g of ethyl chloroformate. The solution is stirred and refluxed for 3 hours. The methanol is distilled off and replaced by 50 ml of water and the reaction mixture is refluxed for 2 hours. The solution is cooled and filtered and the residue is washed with water and recrystallised from aqueous acetic acid, yielding 2-carboethoxyamino-5(6)-(4-methyl-2-n-pentylamino-5-thiazoloyl)-benzimidazole, which melts at 220°–224°.

The starting material is prepared as follows: A mixture of 8.7 g of ethyl imidoacetate and 12.9 g of n-pentyl isothiocyanate is kept at 60° for 4 hours. A mixture of 21 g of the resulting crude adduct with 27 g of 4-chloro-3-nitro-phenacyl bromide in 150 ml of isopropanol is refluxed for 2 hours and the solvent is evaporated. The product is rendered basic with sodium bicarbonate, extracted with ethyl acetate and recrystallised from a mixture of ethyl acetate and hexane, yielding 4-chloro-3-nitro-1-(4-methyl-2-n-pentylamino-5-thiazoloyl)-benzene, which melts at 99°–104°.

A solution of 9 g of the above chlorine compound in 150 ml of ethanolic ammonia is heated at 80° in a bomb tube for 24 hours and cooled and the solvent is evaporated off. Water is added to the residue, the mixture is filtered and the material on the filter is dried and recrystallised from an ethyl acetate/hexane mixture, yielding 1-amino-2-nitro-4-(4-methyl-2-n-pentylamino-5-thiazoloyl)-benzene, which melts at 165°–169°.

EXAMPLE 6

The reagent is prepared analogously to Example 1, using 1.4 g of S-methyl-isothiourea sulfate and 1.2 g of ethyl chloroformate as the starting materials. A solution of 1.8 g of 1,2-diamino-4-(4methyl-2-allylamino-5-thiazoloyl)-benzene dihydrochloride in 20 ml of water and then a solution of 1.4 g of sodium acetate trihydrate in 4 ml of water are added to the resulting solution. The reaction mixture is refluxed for 2 hours, cooled and filtered. The resulting precipitate is washed with water and then with hot methanol. The product is purified by dissolving in 2-normal hydrochloric acid and precipitating with ammonia, yielding 2-carboethoxyamino-5(6)-(4-methyl-2-allylamino-5-thiazoloyl)-benzimidazole, which melts at 210°–219° (decomposition).

The starting material is prepared as follows: A mixture of 8.7 g of ethyl imidoacetate and 10 g of allyl isothiocyanate is kept at 60° for 4 hours. 10 g of the resulting crude adduct and 15 g of 4-chloro-3-nitrophenacyl bromide in 80 ml of isopropanol are refluxed for 2 hours and the solvent is evaporated off. The product is rendered basic and extracted with ethyl acetate. The solvent is evaporated off and the residue is recrystallised from a mixture of ethyl acetate and hexane, yielding 4-chloro-3-nitro-1-(4-methyl-2-allylamino-5-thiazoloyl)-benzene, which melts at 154°–156°.

A solution of 4.5 g of the above chlorine compound in 200 ml of ethanolic ammonia is heated at 120° in a bomb tube for 12 hours, cooled and filtered. The residue is treated with water, dried and recrystallised from aqueous acetic acid, yielding 1-amino-2-nitro-4-(4-methyl-2-allylamino-5-thiazoloyl)-benzene, which melts at 250°–252°.

The last-mentioned nitro compound is reduced analogously to Example 1 with 8 g of stannous chloride dihydrate in 50 ml of acetic acid and yields 1,2-diamino-4-(4-methyl-2-allylamino-5-thiazoloyl)-benzene, which is isolated in the form of the dihydrochloride. The product shrinks at 250° and does not melt up to 350°.

EXAMPLE 7

2.8 g of 1-amino-2-nitro-4-(4-methyl-2-anilino-5-thiazoloyl)-benzene are reduced analogously to Example 1 with 15 g of stannous chloride in 60 ml of acetic acid and the resulting oily diamine is used in the subsequent cyclisation.

A solution of 2.8 g of the above diamine in 50 ml of methanol is added to a reagent solution which has been prepared beforehand (analogously to Example 1) from 2.8 g of S-methyl-isothiourea sulfate and 2.2 g of ethyl chloroformate. The solution is stirred and refluxed for 3 hours. The reaction mixture is cooled and filtered and the residue is washed with water and recrystallised from aqueous acetic acid, yielding 2-carboethoxyamino-5(6)-(4-methyl-2-anilino-5-thiazoloyl)-benzimidazole, which melts at 250°–255° (decomposition).

The starting material is prepared as follows: A mixture of 8.7 g of ethyl imidoacetate and 13.5 g of phenyl isothiocyanate is kept at 60° for one hour and triturated with hexane and the residue is filtered off. The adduct, which melts at 96°–98°, is obtained. It is recrystallised from a mixture of ethyl acetate/hexane.

10 g of the adduct and 13 g of 4-chloro-3-nitrophenacyl bromide in 100 ml of isopropanol are refluxed for 2 hours. The solvent is removed in vacuo and the residue is rendered basic with sodium bicarbonate solution and extracted with ethyl acetate. The extract is dried, concentrated and treated with hexane, yielding 4-chloro-3-nitro-1-(4-methyl-2-anilino-5-thiazoloyl)-benzene, which melts at 162°–165°.

A solution of 3.5 g of the above chlorine compound in 50 ml of ethanolic ammonia is heated at 80° in a bomb tube for 24 hours. The solution is cooled, concentrated to a small volume and filtered. The residue is washed with water and recrystallised from aqueous acetic acid, yielding 1-amino-2-nitro-4-(4-methyl-2-anilino-5-thiazoloyl)-benzene, which melts at 235°–239°.

EXAMPLE 8

The reagent is prepared in situ analogously to Example 1 but methyl chloroformate is used in place of ethyl chloroformate: 8.4 g of S-methyl-isothiourea sulfate and 5.7 g of methyl chloroformate.

A solution of 9.1 g of 1,2-diamino-4-(4-methyl-2-n-butylamino-5-thiazoloyl)-benzene (which is prepared analogously to Example 3) in 200 ml of methanol is added to the resulting solution and the mixture is refluxed for 4 hours. After cooling, the precipitate is filtered off, washed with hot methanol and purified by dissolving in 2 normal hydrochloric acid and precipitating with ammonia, yielding 2-carbomethoxyamino-5(6)-(4-methyl-2-n-butylamino-5-thiazoloyl)-benzimidazole, which melts at 241°–243° (decomposition).

EXAMPLE 9

The reagent is prepared in situ analogously to example 1, using 1.7 g of S-methyl-isothiourea sulfate and 1.4 g of ethyl chloroformate. First a solution of 2 g of 1,2-diamino-4-(4-ethyl-2-methylamino-5-thiazoloyl)-benzene dihydrochloride in 20 ml of water and then a solution of 1.7 g of sodium acetate trihydrate in 5 ml of water are added to the resulting solution. The reaction mixture is stirred and boiled under reflux for 2 hours, cooled and filtered. The residue is washed with water and then with hot methanol and purified by dissolving in 2 normal hydrochloric acid and precipitating with ammonia, yielding 2-carboethoxyamino-5(6)-(4-ethyl-2-methylamino-5-thiazoloyl)-benzimidazole hemihydrate, which melts at 204°–208° (decomposition).

The starting material is prepared as follows: A mixture of 12 g of ethyl imidopropionate and 8.4 g of methyl isothiocyanate is kept at 70° for 2 hours. 20.4 g of the resulting crude adduct and 30 g of 4-chloro-3-nitro-phenacyl bromide in 150 ml of isopropanol are refluxed for 2 hours and the solvent is evaporated off. The product is rendered basic and extracted with methylene chloride. The extract is dried and evaporated and the residue is recrystallised from a mixture of ethyl acetate and hexane, yielding 4-chloro-3-nitro-1-(4-ethyl-2-methylamino-5-thiazoloyl)-benzene, which melts at 186°–190°.

A solution of 4 g of the above chlorine compound in 100 ml of ethanolic ammonia is heated at 120° in a steel tube for 8 hours and cooled and the solvent is evaporated. The residue is digested with water, the mixture is filtered and the material on the filter is recrystallised from aqueous isopropanol, yielding 1-amino-2-nitro-4-(4-ethyl-2-methylamino-5-thiazoloyl)-benzene, which melts at 210°–215°.

5 g of the above nitro compound are reduced analogously to Example 1 with 25 g of stannous chloride in 100 ml of acetic acid. The product is converted to its dihydrochloride using ethanolic hydrogen chloride. After triturating with hot isopropanol, 1,2-diamino-4-(4-ethyl-2-methylamino-5-thiazoloyl)-benzene dihydrochloride is obtained, which melts at 231°–236° (decomposition).

EXAMPLE 10

5.5 g of 1-amino-2-nitro-4-(4-ethyl-2-ethylamino-5-thiazoloyl)-benzene are reduced analogously to Example 1 with 30 g of stannous chloride in 100 ml of acetic acid. The product is converted to its dihydrochloride using hydrogen chloride in isopropanol and this product is filtered off and used immediately for the subsequent cyclisation.

A solution of 2 g of the above dihydrochloride of 1,2-diamino-4-(4-ethyl-2-ethylamino-5-thiazoloyl)-benzene in 20 ml of water is added to a reagent solution which has been prepared beforehand (analogously to Example 1) from 1.7 g of S-methyl-isothiourea sulfate and 1.4 g of ethyl chloroformate, and 1.7 g of sodium acetate trihydrate in 4 ml of water are then added to the mixture. The mixture is stirred and boiled under reflux for 2 hours, cooled and filtered. The residue is washed with water and hot methanol and purified by dissolving in B 2-normal hydrochloric acid and precipitating with ammonia, yielding 2-carboethoxyamino-5(6)-(4-ethyl-2-ethylamino-5-thiazoloyl)-benzimidazole, which melts at 217°–220°.

The starting material is prepared as follows: A mixture of 10 g of ethyl imidopropionate and 10 g of ethyl isothiocyanate is heated at 70° for 2 hours and the crude adduct is used in the subsequent reaction. A mixture of 13.5 g of the said product and 21 g of 4-chloro-3-nitro-phenacyl bromide in 150 ml of isopropanol is refluxed for 2 hours, cooled and filtered. The filtrate is evaporated in vacuo and the residue is rendered basic with sodium bicarbonate solution and extracted with ethyl acetate. The extract is dried and evaporated and the residue is recrystallised from a mixture of ethyl acetate and hexane, yielding 4-chloro-3-nitro-1-(4-ethyl-2-ethylamino-5-thiazoloyl)-benzene, which melts at 149°–152°.

A solution of 8 g of the above chlorine compound in 150 ml of ethanolic ammonia is heated at 120° in a steel tube for 14 hours. The reaction mixture is cooled and the solvent is evaporated off. The residue is digested with water, the mixture is filtered and the material on the filter is dried and recrystallised from a mixture of ethyl acetate and hexane, yielding 1-amino-2-nitro-4-(4-ethyl-2-ethylamino-5-thiazoloyl)-benzene, which melts at 210°–212°.

EXAMPLE 11

The reagent is prepared in situ analogously to Example 1, using 2.8 g of S-methylisothiourea sulfate and 2.2 g of ethyl chloroformate as the starting materials. A solution of 2.8 g of 1,2-diamino-4-(4-methyl-2-dimethylamino-5-thiazoloyl)-benzene in 80 ml of methanol is added to the resulting solution and the mixture is refluxed for 2 hours. The solution is cooled and evaporated, the residue is digested with water and the mixture is filtered. The residue is washed with hot methanol and purified by dissolving in 2 normal hydrochloric acid and precipitating with ammonia, yielding 2-carboethoxyamino-5(6)-(4-methyl-2-dimethylamino-5-thiazoloyl)-benzimidazole monohydrate, which melts at 270°–275° (decomposition).

The starting material is prepared as follows: A mixture of 3.7 g of N-acetyl-N',N'-dimethyl-thiourea and 7 g of 4-chloro-3-nitro-phenacyl bromide in 100 ml of isopropanol is refluxed for 2 hours, cooled and filtered. The residue is rendered basic and extracted with methylene chloride. The extract is dried and evaporated and the residue is recrystallised from a mixture of ethyl acetate and hexane, yielding 4-chloro-3-nitro-1-(4-methyl-2-dimethylamino-5-thiazoloyl)-benzene, which melts at 165°–169°.

A mixture of 3.5 g of the above chlorine compound and 0.5 ml of ethylene glycol in 40 ml of alcoholic ammonia is heated at 130° in a bomb tube for 16 hours. The product is filtered off, washed with water and recrystallised from a mixture of ethyl acetate and hexane, yielding 1-amino-2-nitro-4-(4-methyl-2-dimethylamino-5-thiazoloyl)-benzene, which melts at 225°–228°.

7 g of the above nitro compound are reduced analogously to Example 1 with 40 g of stannous chloride in 150 ml of acetic acid. The product is extracted with methylene chloride and the extract is dried and evaporated. The residue is recrystallised from isopropanol, yielding 1,2-diamino-4-(4-methyl-2-dimethylamino-5-thiazoloyl)-benzene, which melts at 174°–178°.

EXAMPLE 12

The reagent is prepared in situ analogously to Example 1, using 2.8 g of S-methyl-isothiourea sulfate and 2.2 g of ethyl chloroformate as the starting materials. A solution of 3.8 g of 1,2-diamino-4-(4-methyl-2-pyrrolidinyl-5-thiazoloyl)-benzene dihydrochloride in 20 ml of water and then a solution of 2.8 g of sodium acetate trihydrate in 8 ml of water are added to the resulting solution. The reaction mixture is stirred and refluxed for 2 hours, cooled and filtered. The residue is washed, first with water and then with hot methanol, and purified by dissolving in 2 normal hydrochloric acid and precipitating with ammonia, yielding 2-carboethoxyamino-5(6)-(4-methyl-2-pyrrolidinyl-5-thiazoloyl)-benzimidazole hemihydrate, which melts at 185°–195° (decomposition).

The starting material is prepared as follows: A mixture of 10 g of methyl N-acetyl-dithiocarbamate and 5 g of pyrrolidine in 100 ml of ethanol is kept at 30° for 16 hours, the solvent is evaporated off in vacuo and the residue is recrystallised from a mixture of ethyl acetate and hexane, yielding pyrrolidinothiocarbonylacetamide, which melts at 110°–120°.

A mixture of the last-mentioned thiourea derivative and 16.8 g of 4-chloro-3-nitro-phenacyl bromide in 200 ml of isopropanol is refluxed for 3 hours and evaporated. The residue is digested with water, rendered basic with sodium bicarbonate solution and extracted with ethyl acetate. The extract is dried, concentrated, cooled and filtered, yielding 4-chloro-3-nitro-1-(4-methyl-2-pyrrolidinyl-5-thiazoloyl)-benzene, which melts at 168°–171°.

A solution of 4 g of the above chlorine compound in 100 ml of ethanolic ammonia is heated at 120° in a steel tube for 8 hours, cooled and filtered. The residue is washed with water and recrystallised from aqueous acetic acid, yielding 1-amino-2-nitro-4-(4-methyl-2-pyrrolidinyl-5-thiazoloyl)-benzene, which melts at 245°–248° (decomposition).

6 g of the above nitro compound are reduced analogously to Example 1 with 30 g of stannous chloride in 100 ml of acetic acid. The product is converted to its hydrochloride using hydrogen chloride in ethanol, this product is digested with hot isopropanol and the mixture is filtered, yielding 1,2-diamino-4-(4-methyl-2-pyrrolidinyl-5-thiazoloyl)-benzene dihydrochloride, which melts at 210°–220° (decomposition).

EXAMPLE 13

4 g of 1-amino-2-nitro-4-(2-n-butylamino-5-thiazoloyl)-benzene are reduced analogously to Example 1 with 20 g of stannous chloride in 100 ml of acetic acid. The resulting crude diamine is used in the subsequent cyclisation.

A solution of 4 g of the above diamine in 50 ml of methanol is added to a reagent solution which has been prepared beforehand (analogously to Example 1) from 4.2 g of S-methyl-isothiourea sulfate and 3.2 g of ethyl chloroformate. The solution is stirred and refluxed for 3 hours. The methanol is distilled off and replaced by 50 ml of water and the reaction mixture is refluxed for 2 hours. The solution is cooled and filtered and the precipitate is washed with water. The product is purified by dissolving in 2 normal hydrochloric acid and precipitating with ammonia, yielding 2-carboethoxyamino 5(6)-(2-n-butylamino-5-thiazoloyl)-benzimidazole, which melts at 295°–300° (decomposition).

The starting material is prepared as follows: A mixture of 5 g of N-butyl-thiourea and 15 ml of dimethylformamide dimethyl acetal is refluxed for 6 hours and the excess DMF acetal is evaporated off in vacuo. The residue is used in the subsequent condensation reaction.

7 g of the resulting imidoylthiourea and 11 g of 4-chloro-3-nitro-phenacyl bromide in 100 ml of isopropanol are refluxed for 1 hour. The solvent is evaporated off, the residue is digested with water and ethyl acetate and the mixture is filtered. The solid material is recrystallised from ethyl acetate, yielding 4-chloro-3-nitro-1-(2-n-butylamino-5-thiazoloyl)-benzene, which melts at 192°–194°.

8 g of the above chlorine compound are taken and heated with 150 ml of ethanolic ammonia at 80° in a steel tube for 24 hours. The reaction mixture is cooled and filtered and the residue is washed with water, dried and recrystallised from ethyl acetate, yielding 1-amino-2-nitro-4-(2-n-butylamino-5-thiazoloyl)-benzene, which melts at 198°–203°.

EXAMPLE 14

5 g of 1-amino-2-nitro-4-(2-cyclohexylamino-5-thiazoloyl)-benzene are reduced analogously to Example 1 with 25 g of stannous chloride in 125 ml of acetic acid. The resulting crude diamine is used in the subsequent cyclisation.

A solution of 4.5 g of the above diamine in 50 ml of methanol is added to a reagent solution which has been prepared beforehand (analogously to Example 1) from 4.2 g of S-methyl-isothiourea sulfate and 3.2 g of ethyl chloroformate. The solution is stirred and refluxed for 2 hours. The methanol is then distilled off and replaced by 50 ml of water and the mixture is refluxed for a further 2 hours. The solution is cooled and filtered and the residue is washed with water and purified by dissolving in 2 normal hydrochloric acid and precipitating with aqueous ammonia. The precipitate is filtered off, washed with water, dried, digested with hot ethyl acetate and filtered off again, yielding 2-carboethoxyamino-5(6)-(2-cyclohexylamino-5-thiazoloyl)-benzimidazole, which melts at 216°–219° (decomposition).

The starting material is prepared as follows: A mixture of 5 g of N-cyclohexylthiourea and 10 ml of dimethylformamide dimethyl acetal is refluxed for 6 hours and the excess DMF acetal is removed in vacuo. The residue is digested with hexane and the solid material is recrystallised from a mixture of ethyl acetate and hexane, yielding N,N-dimethyl-N'-cyclohexyl-thiocarbamylformamidine, which melts at 116°–120°.

5 g of the last-mentioned compound and 7 g of 4-chloro-3-nitro-phenacyl bromide in 100 ml of isopropanol are refluxed for 2 hours. The solvent is evaporated off, the residue is digested with water and ether, the mixture is filtered and the material on the filter is recrystallised from ethyl acetate, yielding 4-chloro-3-nitro-1-(2-cyclohexylamino-5-thiazoloyl)-benzene, which melts at 194°–198°.

A solution of 6 g of the last-mentioned compound in 150 ml of ethanolic ammonia is heated at 80° in a steel tube for 24 hours, cooled and filtered. The residue is washed with water and recrystallised from aqueous acetic acid, yielding 1-amino-2-nitro-4-(2-cyclohexylamino-5-thiazoloyl)-benzene, which melts at 245°–250°.

What is claimed is:

1. 2-Carbomethoxyamino-5(6)-(4-methyl-2-n-butylamino-5-thiazoloyl)-benzimidazole and a therapeutically acceptable salt thereof.

2. A therapeutic composition for the treatment of parasitic infections by helminths comprising an effective amount of an anthelmintic active compound of claim 1, together with a pharmaceutically acceptable excipient.

3. A method for the treatment of parasitic infections by helminths which comprises administering to a living body suffering from parasitic infections an effective amount of a compound of claim 1.

* * * * *